United States Patent
Tass et al.

(10) Patent No.: US 9,572,996 B2
(45) Date of Patent: Feb. 21, 2017

(54) DEVICE AND METHOD FOR STIMULATION BY MEANS OF THERMAL STIMULI

(71) Applicant: Forschungszentrum Juelich GmbH, Juelich (DE)

(72) Inventors: Peter Alexander Tass, Juelich (DE); Jean-Christophe Roulet, Ligniéres/Ne (CH); Thomas Von Bueren, Bern (CH); Jean-Noel Fehr, Neuchatel (CH); Urban Schnell, Muenchenbuchsee/Be (CH)

(73) Assignee: Forschungszentrum Juelich GmbH, Juelich (DE)

( * ) Notice: Subject to any disclaimer, the term of this patent is extended or adjusted under 35 U.S.C. 154(b) by 115 days.

(21) Appl. No.: 14/384,480

(22) PCT Filed: Mar. 12, 2013

(86) PCT No.: PCT/EP2013/054984
§ 371 (c)(1),
(2) Date: Sep. 11, 2014

(87) PCT Pub. No.: WO2013/135685
PCT Pub. Date: Sep. 19, 2013

(65) Prior Publication Data
US 2015/0105844 A1    Apr. 16, 2015

(30) Foreign Application Priority Data
Mar. 12, 2012    (DE) ................ 10 2012 005 030

(51) Int. Cl.
*A61N 5/06*    (2006.01)
*A61N 5/00*    (2006.01)
(Continued)

(52) U.S. Cl.
CPC .............. *A61N 5/0625* (2013.01); *A61N 5/00* (2013.01); *A61N 5/0622* (2013.01);
(Continued)

(58) Field of Classification Search
CPC .. A61N 5/0625; A61N 5/00; A61F 2007/0088
(Continued)

(56) References Cited

U.S. PATENT DOCUMENTS

| | | | | |
|---|---|---|---|---|
| 4,930,504 A | * | 6/1990 | Diamantopoulos | .. A61N 5/0616 250/494.1 |
| 5,755,751 A | * | 5/1998 | Eckhouse | ............ A61B 18/203 606/9 |

(Continued)

FOREIGN PATENT DOCUMENTS

| | | |
|---|---|---|
| CN | 101115524 A | 1/2008 |
| CN | 10 2009 025 407 A1 | 12/2010 |

(Continued)

OTHER PUBLICATIONS

Gary Chang, Tile, Jul. 2, 2007, Coroflot, www.coroflot.com/C-DESIGN/Tile.*

(Continued)

*Primary Examiner* — Lynsey Crandall
*Assistant Examiner* — Jonathan Kuo
(74) *Attorney, Agent, or Firm* — Arent Fox LLP

(57) ABSTRACT

The invention relates to a device for the stimulation of thermal receptors in the skin of a patient by means of thermal stimuli. The device comprises a plurality of noninvasive stimulation units for irradiating the skin of the patient with electromagnetic radiation, wherein thermal stimuli are produced by absorption of the electromagnetic radiation in the skin of the patient and the wavelength range of the electromagnetic radiation emitted by the stimulation units (Continued)

can be adjusted. The device also comprises a control unit for controlling the stimulation units.

9 Claims, 13 Drawing Sheets

(51) Int. Cl.
*A61F 7/00* (2006.01)
*A61N 5/067* (2006.01)

(52) U.S. Cl.
CPC . *A61F 2007/0088* (2013.01); *A61N 2005/067* (2013.01); *A61N 2005/0651* (2013.01); *A61N 2005/0652* (2013.01); *A61N 2005/0653* (2013.01); *A61N 2005/0659* (2013.01)

(58) Field of Classification Search
USPC .......................................................... 607/90
See application file for complete search history.

(56) References Cited

U.S. PATENT DOCUMENTS

| 6,974,224 | B2 | 12/2005 | Thomas-Benedict | |
| 7,492,987 | B2* | 2/2009 | Yeik | A61B 18/24 |
| | | | | 385/31 |
| 8,083,784 | B2 | 12/2011 | Van Zuylen | |
| 2005/0085875 | A1 | 4/2005 | Van Zuylen | |
| 2007/0198004 | A1 | 8/2007 | Altshuler et al. | |
| 2007/0264455 | A1 | 11/2007 | Chin et al. | |
| 2008/0046025 | A1 | 2/2008 | Tass | |
| 2008/0077198 | A1* | 3/2008 | Webb | A61N 5/0618 |
| | | | | 607/88 |
| 2009/0018622 | A1 | 1/2009 | Asvadi et al. | |
| 2010/0045175 | A1 | 2/2010 | Mathai et al. | |
| 2010/0324631 | A1 | 12/2010 | Tass et al. | |
| 2011/0201977 | A1 | 8/2011 | Tass et al. | |
| 2013/0041296 | A1 | 2/2013 | Tass et al. | |

FOREIGN PATENT DOCUMENTS

| CN | 102186538 A | 9/2011 |
| DE | 102010000390 A1 | 8/2011 |
| JP | 2009-532079 A | 9/2009 |
| WO | WO 2011/098082 A | 8/2011 |
| WO | WO 2011/127918 A | 10/2011 |

OTHER PUBLICATIONS

International Search Report issued for PCT/EP2013/054984, mail date Jun. 5, 2013.
R.K. Hobbie and J. Roth; "Atoms and Light"; Intermediate Physics for Medicine and Biology, Fourth Edition, Springer 2007 (cover pp. 1-4), pp. 359-399.
S.L. Jacques; "Skin Optics", Oregon Medical Laser Center News (Jan. 1998); http://omlc.orq/news/jan98/skinoptics.html.
P.A. Tass; "A model of desynchronizing deep brain stimulation with a demand-controlled coordinated reset of neural subpopulations"; Biological Cybernetics 89, 2003, pp. 81-88.
A. Benninghoff et al.; "Lehrbuch der Anatomie des Menschen. Dargestellt unter Bevorzugung funktioneller Zusammenhänge. 3. Bd. Nervensystem, Haut und Sinnesorgane", [Textbook of Human Anatomy. Presented With Emphasis on Functional Relatonships. 3rd vol., Nervous System, Skin and Sensory Organs], Urban und Schwarzenberg, Munich 1964, pp. 126-137.

* cited by examiner

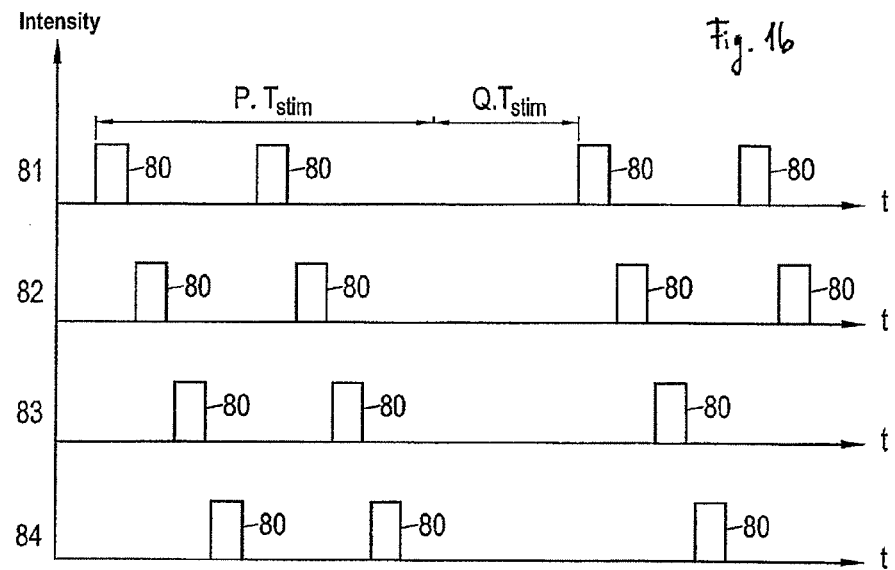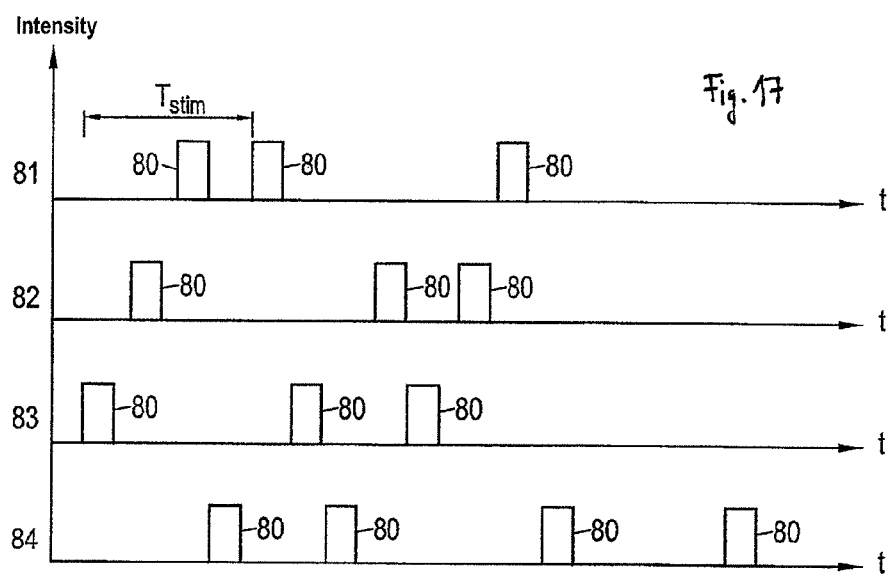

ously active. This means that a large number of neurons forms synchronous action potentials; the associated neurons fire excessively synchronously. In contrast to this, with regard to healthy patients, the neurons trigger in a qualitatively different manner in these brain regions, e.g. in a non-correlated manner.

DEVICE AND METHOD FOR STIMULATION BY MEANS OF THERMAL STIMULI

The invention relates to an apparatus and to a method for the stimulation of thermal receptors lying in the skin of a patient with thermal stimuli.

For many diseases in which an increased neuronal synchronization is present, such as e.g. strongly pronounced dysfunctions following a stroke or an irritable bowel syndrome, there is currently no satisfactory therapy. It is characterizing for these diseases that healthy nerve cell activity is interfered with and/or limited as a consequence of the pathologically excessive synchronization in the nervous system and in this way of the associated pathologically increased interconnection of the concerned network of neurons and that pathological patterns in space and time of the nerve cell activity are established (e.g. in the framework of a maladaptation).

Having regard to these diseases specific nerve cell networks, e.g. in the brain or in enteral ganglias, are pathologically, typically excessively, synchronously active. This means that a large number of neurons forms synchronous action potentials; the associated neurons fire excessively synchronously. In contrast to this, with regard to healthy patients, the neurons trigger in a qualitatively different manner in these brain regions, e.g. in a non-correlated manner.

The invention is based on the object of providing an apparatus, as well as a method for the stimulation with thermal stimuli in which a more efficient desynchronization and a more long-term persistent unlearning of pathologically synaptic networking can be achieved with respect to the state of the art.

The object underlying the invention is satisfied by the features of the independent claims. Advantageous embodiments and designs of the invention are stated in the dependent claims.

The invention will be described in detail in the following in an exemplary manner with reference to the drawing. In these there is shown:

FIG. 1 a schematic illustration of an apparatus for the stimulation of thermal receptors lying in the skin of a patient with thermal stimuli during the operation;

FIG. 2 an illustration of the coefficient of absorption of water;

FIG. 3 an illustration of the calculated percentage of the absorbed radiation with regard to the wavelength for different absorption depths;

FIGS. 4A to 4D schematic illustrations of different embodiments of a stimulation unit for the generation of electromagnetic radiation with different wavelengths;

FIGS. 5A to 5F schematic representations of different embodiments of a stimulation unit for the formation of the emitted electromagnetic radiation;

FIGS. 6A to 6I schematic illustrations of different optical elements for the generation of homogeneously distributed electromagnetic radiation;

FIGS. 7A to 7C schematic illustrations of an embodiment of a stimulation unit for the generation of thermal stimuli;

FIGS. 8 to 10 schematic illustrations of embodiments of an apparatus for the thermal stimulation with one or more lasers or other heat emitters for the generation of electromagnetic radiation;

FIGS. 11A and 11B schematic illustrations of an embodiment of an apparatus for the thermal stimulation with a plurality of organic light emitting diodes;

FIGS. 12A to 13B schematic illustrations of embodiments of an apparatus for the thermal stimulation by means of stimulation units which can be mechanically and electrically connected to one another;

FIG. 14 a schematic illustration of a thermal stimuli;

FIG. 15 a schematic illustration of a coordinated reset stimulation ("CR stimulation") by means of thermal stimuli; and FIGS. 16 and 17 schematic illustrations of further CR stimulations by means of thermal stimuli.

FIG. 1 schematically shows an apparatus 1 for the stimulation of thermal receptors lying in the skin of a patient with thermal stimuli. The apparatus 1 in particular is a photodynamic stimulator. The apparatus 1 includes a plurality of stimulation units 2 for the irradiation of the skin of the patient with electromagnetic radiation. The wavelength range of the electromagnetic radiation emitted by the stimulation units 2 can be set. Furthermore, a control unit 3 for the control of the stimulation units 2 is provided. The stimulation units 2 and in particular also the control unit 3 are non-invasive units, this means that during the operation of the apparatus 1 they are present outside of the body of the patient and are not operatively implanted into the body of the patient. The plurality of stimulation units 2 facilitates the fact that different receptive regions of the skin are stimulated via the individual stimulation units 2 coordinated in time and space.

The electromagnetic radiation emitted by the stimulation units 2 is absorbed in the skin of the patient. Through the absorption of the electromagnetic radiation regions of the skin are heated and thermal receptors 4 lying in the skin are ideally stimulated with thermal stimuli thereby. The thermal receptors 4 are present—as is schematically indicated in FIG. 1—directly below the epidermis 5 and the dermal papilla in the dermis 6 (typically at a depth of approximately 150 µm beneath the skin surface). Preferably the wavelength of the electromagnetic radiation emitted by the stimulation unit 2 is set in such a way that the electromagnetic radiation is absorbed by the region 7 of the dermis 6 in which the thermal receptors 4 are present and that none or only a little of the electromagnetic radiation is absorbed by the epidermis 5.

Infrared radiation with a wavelength in the range of 780 nm to 1 mm (and in particular in the near infrared range of 780 nm to 3,000 nm) is the most suitable form of electromagnetic radiation for the thermal stimulation, as it is strongly absorbed by the dermis. For a wavelength of greater than 1,000 nm, the water contained in the blood is primarily responsible for the absorption of the radiation in the dermis. As the illustration of the coefficient of absorption of water in FIG. 2 shows, water has a high capability of absorption for radiation with a wavelength of more than 1,000 nm. As the epidermis includes no blood vessels, the water concentration is lower there than in the dermis. This enables an increase in heat of the dermis for at the same time only a slight increase in heat of the epidermis through the selection of a suitable wavelength spectrum.

Ultraviolet radiation is less suitable for the thermal stimulation, as the skin can easily be damaged by this highly energetic radiation. Moreover, the ultraviolet radiation is strongly absorbed by the melanin contained in the epidermis. The light visible for humans does not include these disadvantages, however, is absorbed comparatively poorly in the epidermis and the dermis.

On the use of infrared radiation for the generation of thermal stimuli it has to be noted that water is also present in the epidermis and that the radiation is thus also absorbed there. For this reason it is required to find the correct balance between a high coefficient of absorption, which leads to a strong absorption of the radiation in a comparatively thin layer, but only for a low penetration depth of the radiation, and to a low coefficient of absorption, which enables a deeper penetration of the radiation (and thus to an absorption in the dermis), as well as to an absorption of the radiation in a thicker layer. In order to visualize this association the calculated percentage of the absorbed radiation is applied with regard to the wavelength for different absorption depths (with one having to assume that the absorption process in water is essential for the stimulation of the thermal receptors).

In accordance with the invention it is provided that the wavelength of the applied electromagnetic radiation is set in such a way that the thermal receptors lying in the dermis are ideally stimulated. As the absorption behavior of the skin is individually different, the wavelength and/or the wavelength range is determined advantageously for each patient prior to the therapy, with which wavelength and/or wavelength range the best possible stimulation results can be achieved.

Infrared radiation sources known to the skilled person can be used as radiation sources for the generation of the electromagnetic radiation. Examples of this are light emitting diodes (LEDs), organic light emitting diodes (OLEDs), super-luminescence light emitting diodes (SLEDs), semiconductor laser diodes, such as e.g. DH (Double Heterostructure)-lasers, quantum well lasers, quantum cascade lasers, SCH (Separate Confinement Heterostructure)-lasers, DFB (Distributed Feedback)-lasers and VCSEL (Vertical Cavity Surface-Emitting)-lasers as well as gas lasers and solid state lasers. In particular Ho:YAG (Holmium:YAG) lasers having a wavelength of 2.1 µm and GaAs laser diodes in the wavelength range of 1.3 to 1.5 µm are suitable as radiation sources in order to stimulate the thermal receptors in a depth of approximately 100 to 200 µm beneath the skin surface and in particular in a range of about 150 µm.

FIGS. 4A to 4D schematically show different embodiments of a stimulation unit 2 with which the radiation of a desired spectral range can be produced in order to be able to ideally stimulate the thermal receptors lying in the skin of the patient.

The radiation source 8 shown in FIG. 4A generates electromagnetic radiation with a wavelength distribution $\lambda_{RS}$.

In FIG. 4B the radiation emitted by the radiation source 8 runs through an optical filter 10, whereby certain parts of the spectrum are eliminated and a wavelength distribution $\lambda_F$ results at the output of the optical filter 10. Different optical filters 10 can be provided in order to be able to generate radiation with different wavelength distributions $\lambda_F$. The stimulation unit 2 can be configured in such a way that selectively one of the optical filters 10 (or also none of the optical filters 10) are switched in front of the radiation source 8 in order to generate an ideal wavelength range thereby for the stimulation of the thermal receptors.

FIG. 4C shows a fluorescing material 11 by means of which the spectrum generated by the radiation source 8 is displaced and the wavelength distribution $\lambda_C$ shown in FIG. 4C is obtained. Different fluorescing materials 11 can be made available which can selectively be switched in front of the radiation source 8 in order to generate different wavelength distributions $\lambda_C$.

FIG. 4D shows an embodiment of the stimulation unit 2 with a radiation source 8 whose radiation spectrum can be set by the control unit 3. For example the radiation source 8 can be a tunable laser. In FIG. 4D three different wavelength distributions $\lambda_{RS}(t_1)$, $\lambda_{RS}(t_2)$ and $\lambda_{RS}(t_3)$ are illustrated by way of example. Through a suitable setting of the radiation source 8 the position and extent of the region 7 in the dermis shown in FIG. 1, in which an absorption of the radiation and in this way a temperature rise in the tissue is brought about, can be set.

The radiation emitted by the radiation source 8 can be formed through the use of corresponding optical elements, as will be explained in the following by way of example with reference to the FIGS. 5A to 5F. In the FIGS. 5A to 5F the generated beam power $E_e$ at the skin surface is illustrated beside the different optical elements.

Whereas FIG. 5A shows the beam source 8 without optical elements for beam forming, a mirror 15 is arranged in the optical path of the radiation source 8 in FIG. 5B which simultaneously acts as a lens.

In FIG. 5C the radiation of the radiation source 8 is coupled into a light guide 17 by means of a lens 16. The radiation output by the light guide 17 runs through a further lens 18 which generates a homogeneously distributed beam power over a certain skin region.

Whereas the positions of the optical elements shown in the FIGS. 5B and 5C are fixed, the positions of the optical elements shown in the FIGS. 5D to 5F can be varied.

In FIG. 5D a convex lens 19 is shown which can be displaced along the z-axis. The radiation power $E_e$ generated thereby at the skin surface is illustrated for two positions of the lens 19.

It is plausible to use a cooling system, such as, for example, a ventilator or a thermal electrical cooler for cooling the epidermis in order to thereby increase the effectivity of the thermal stimulation. As the thermal receptors primarily react to temperature gradients, it can be advantageous to again remove the heat introduced into the stimulation region by the thermal stimuli from the stimulation region between subsequent stimulation stages.

In order to exclude injuries of the patient by locally overheated beam powers it is advantageous to shape the radiation in such a way that it is distributed over a certain surface and that a predefined boundary value of the beam power is exceeded at no position. Ideally, the beam power is homogeneously distributed as far as possible over a certain region at the skin of the patient. For this purpose, optical elements, for example shown in the FIGS. 6A to 6H, can be used, wherein the optical elements are illustrated at the left and the right hand side of the Figures from respectively different viewing directions.

Figure 1:
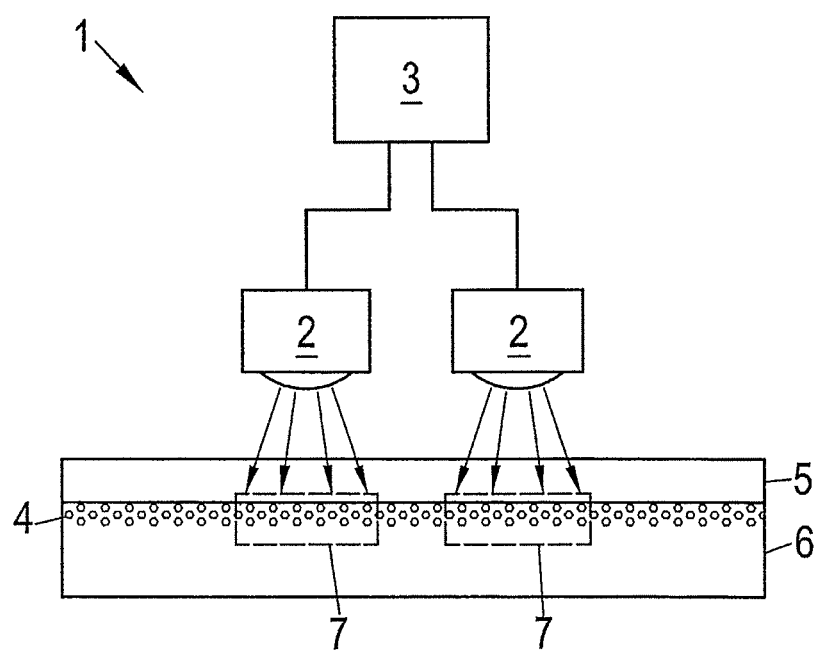
Figure 2:
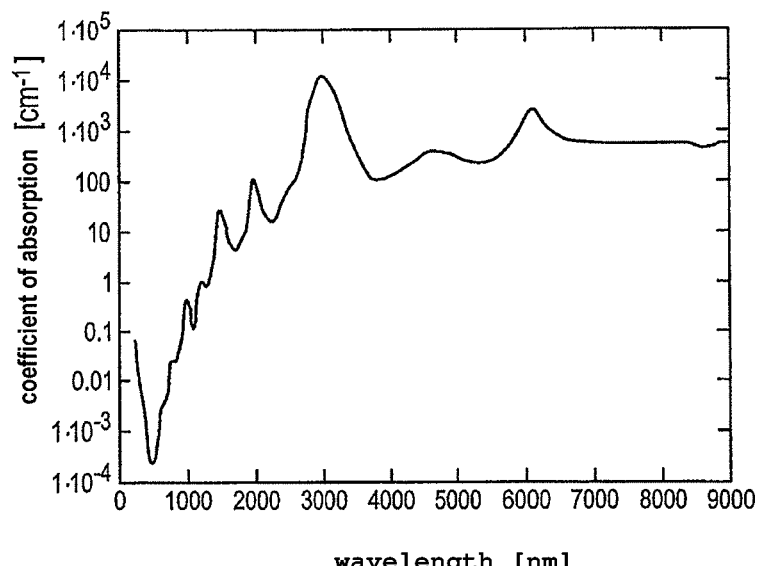
Figure 3:
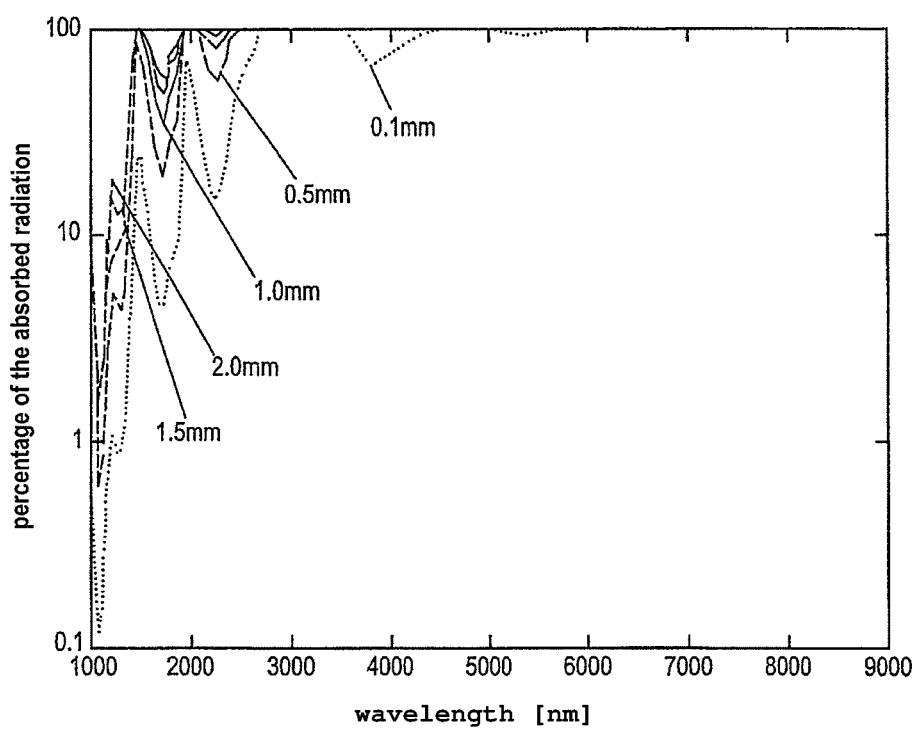
Figure 4D:
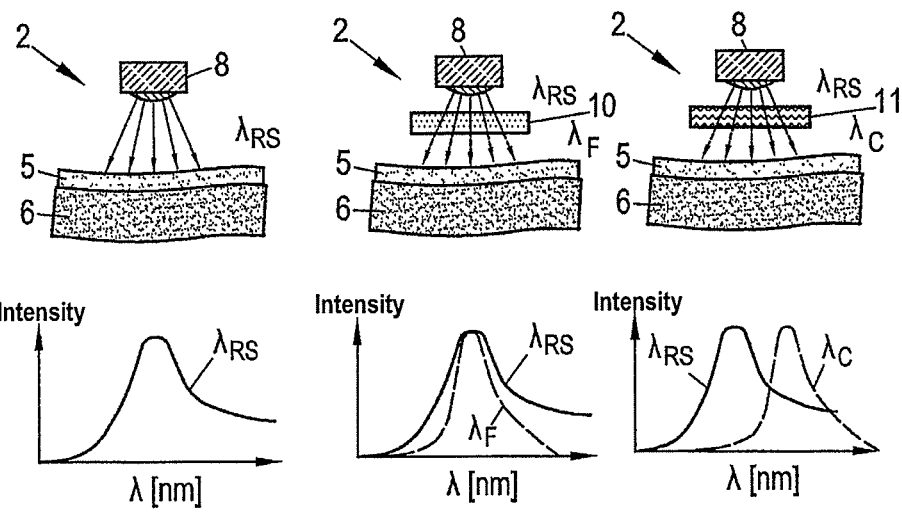
Figure 4D:
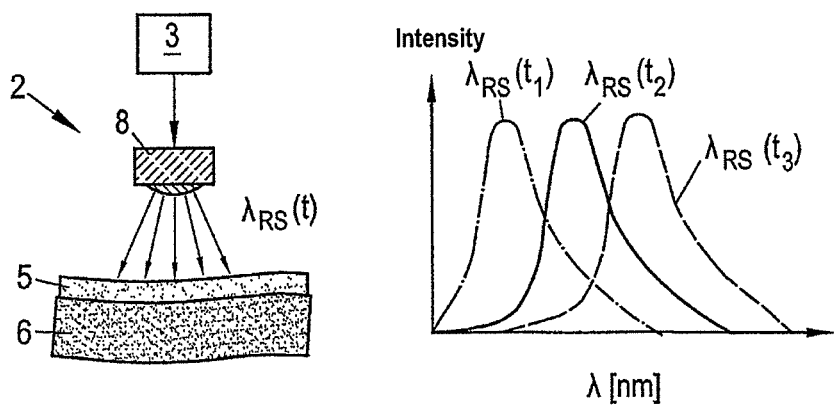
Figures 5A, 5B, 5C:
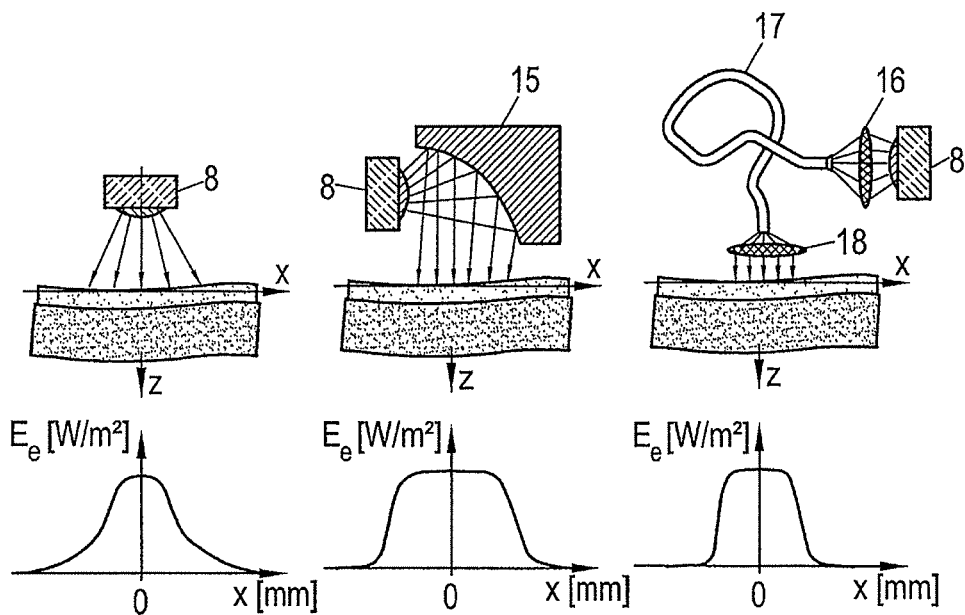
FIG. 5E shows a tiltable and deformable mirror system 20 which permits a variation both of the position of irradiation as well as of the radiation power.
FIG. 5F shows a mechanical closure 21 which can be configured e.g. as an aperture, a rotating closure, a slider or the like and which can either let the radiation generated by the beam source pass completely or not pass at all.
Figures 5D, 5E, 5F:
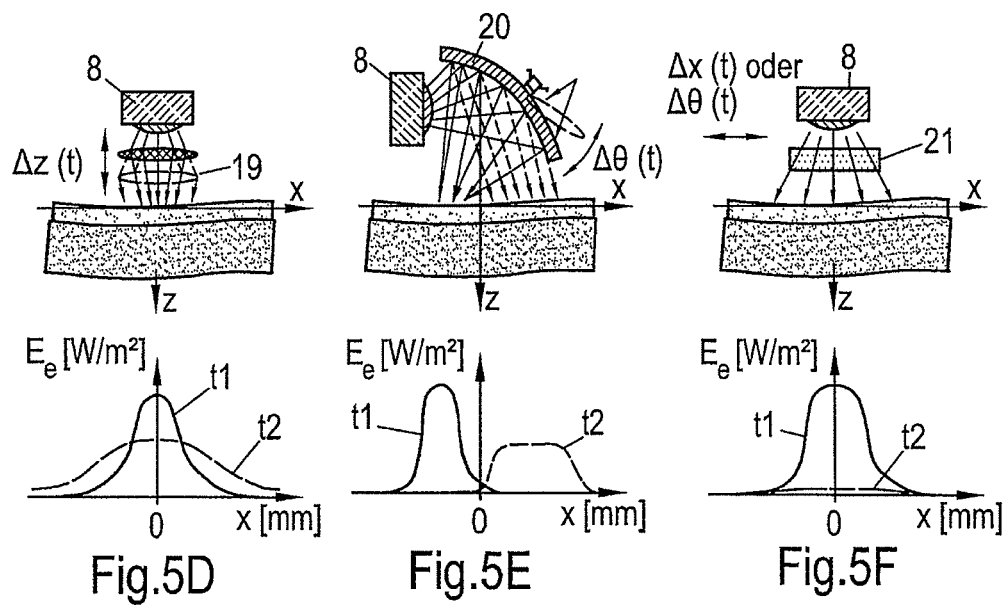
Figure 6A:
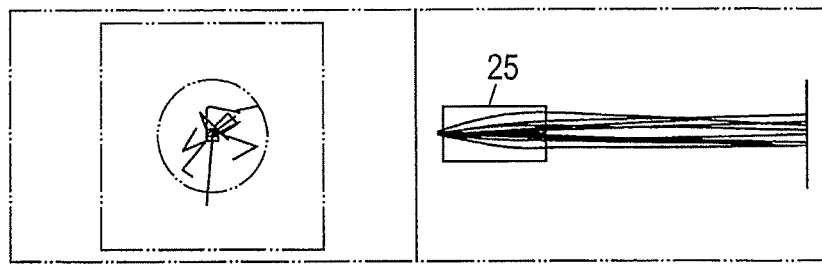
Figure 6B:
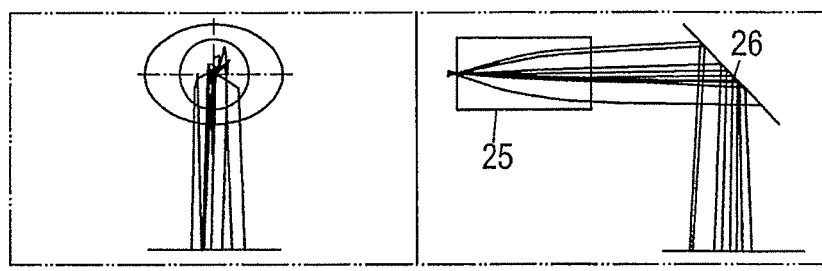

FIGS. 6A and 6B show a gradient lens 25 (also named GRIN lens or gradient index lens) which collimates radiation generated by one of the radiation sources. A mirror 26 is additionally arranged in the optical path in FIG. 6B with which the radiation is aligned into the target area. Through the use of the mirror 26 the stimulation unit can be configured comparatively flat.

Figure 6C:
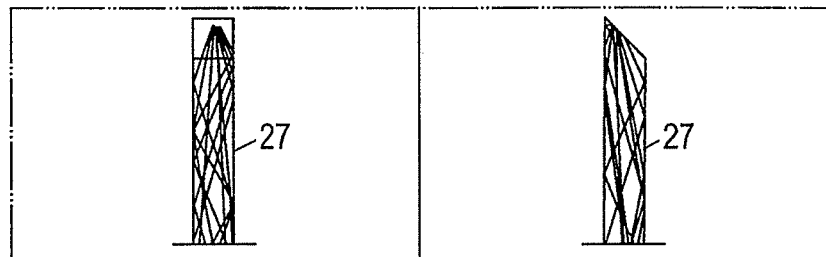
Figure 6D:
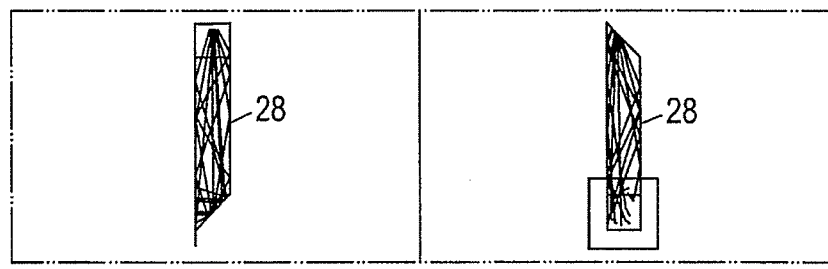

FIGS. 6C and 6D show light guides 27, 28 respectively from two different sides. Both light guides 27, 28 have a quadratic cross-section, but their cross-sections can also have a different geometric shapes. Furthermore, the light guides 27, 28 have a surface chamfered by 45° at one of their ends at which the beam source can be fastened. At the other end of the light guide 27, 28 the radiation again exits with a very precise and homogeneous distribution. This end can be brought into contact with the skin of the patient. The light guide 28 moreover has a chamfered surface at the lower end which results in the radiation laterally exiting from the light guide 28.

Figure 6E:
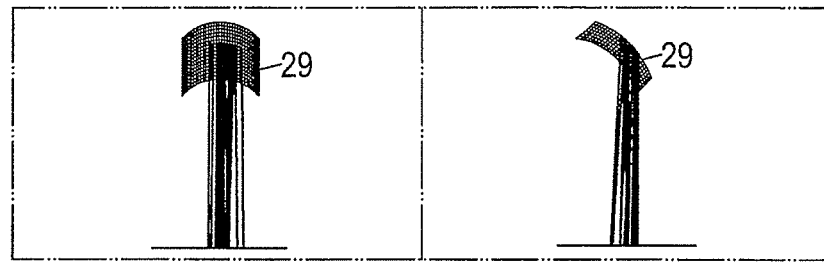
Figure 6F:
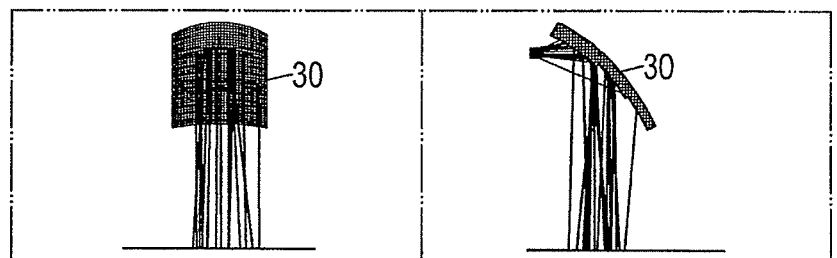

FIGS. 6E and 6F show one and three toroidal mirrors 29, 30 respectively with different radii of curvature in the directions of the x- and y-axes, by means of which a precise beam forming can be achieved.

Figure 6G:
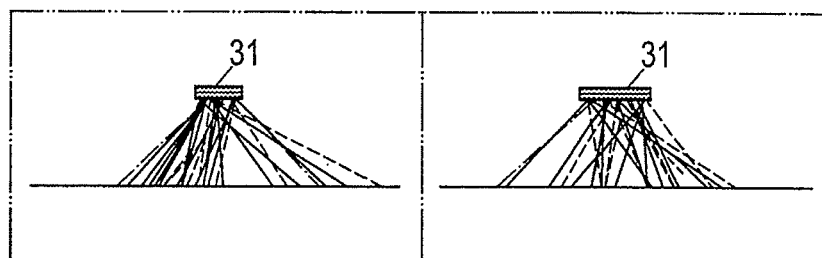

FIG. 6G shows an optical element 31 having a refractive upper side, as well as reflecting side surfaces. The lower side of the optical element 31 scatters the radiation in the direction of the target position. The scattering lower side can bring about a Gaussian distribution of the radiation.

Figure 6H:
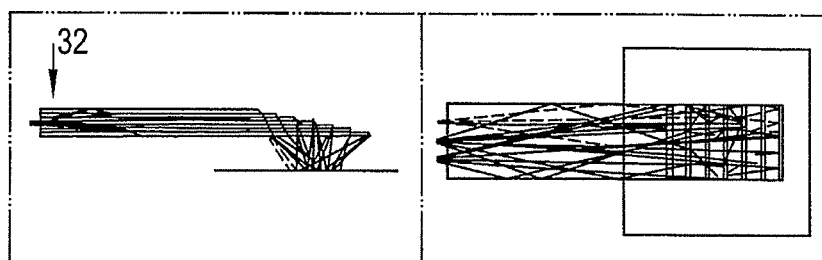

FIG. 6H shows an arrangement 32 having a plurality of optical elements which respectively have different lengths and angles. The arrangement 32 allows the generation of a complex beam extent.

Figure 6I:
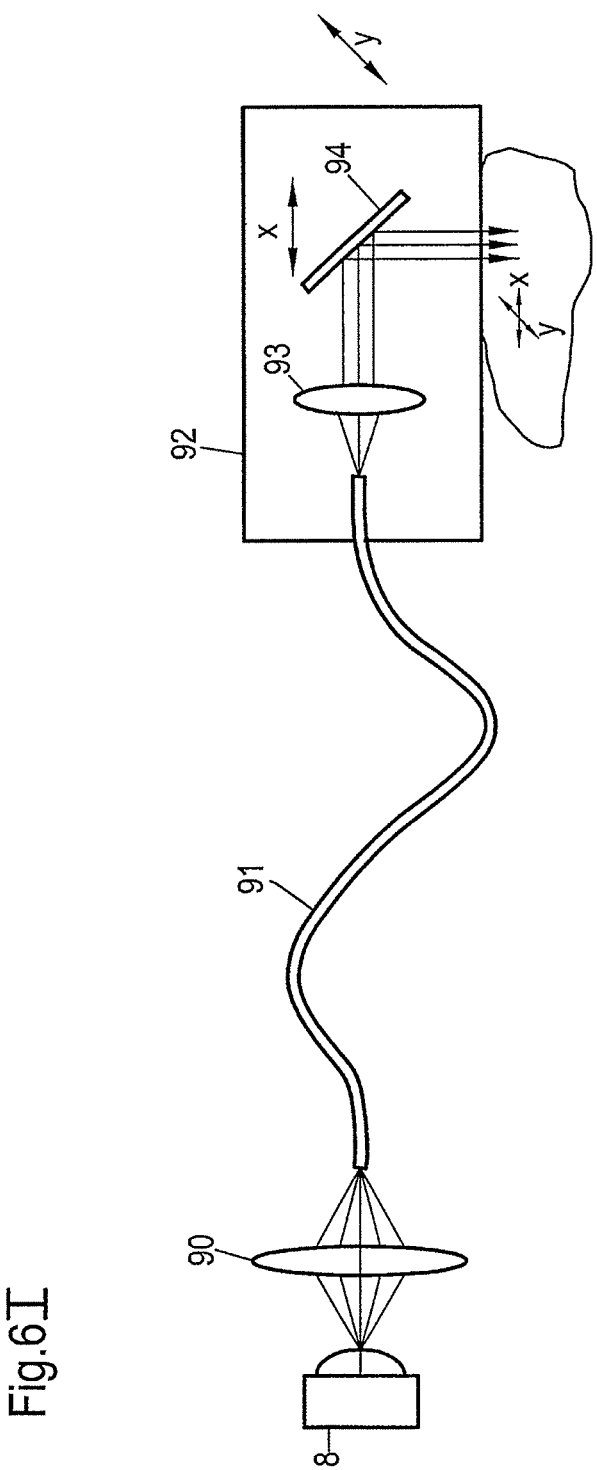

FIG. 6I shows an apparatus having a radiation source 8 for the generation of electromagnetic radiation which can be coupled into a light guide 91 by means of a lens 90. The light guide 91 guides the electromagnetic radiation to a scanner 92 in which a lens 93 and a mirror 94 displaceable in the x- and y-directions, or a different correspondingly adjustable element, is present. Through the adjustment of the position of the mirror 94, a certain skin position can targetedly be stimulated. Furthermore, different positions of a certain region of the skin can successively be stimulated.

Figures 7A, 7B, 7C:
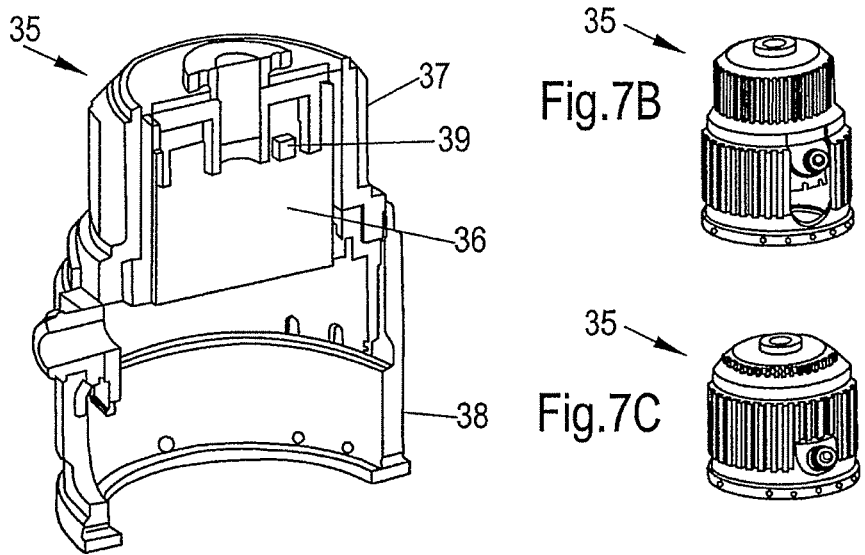

FIG. 7A shows a stimulation unit 35 for the generation of thermal stimuli by means of electromagnetic radiation in a partly sectioned view. In the FIGS. 7B and 7C the stimulation unit 35 is shown in two different operating states. A filament-like infra-red radiation source 36 integrated into the stimulation unit 35 serves for the generation of the electromagnetic radiation. The infrared radiation source 36 is introduced into a cylindrical housing 37 which is connected to a cylindrical spacer 38 via a thread. For the treatment of a patient the stimulation unit 35 is placed onto the skin of the patient with the lower side of the spacer 38. The spacing between the radiation source 36 and the skin of the patient can be adjusted (FIGS. 7B and 7C show different spacings). Furthermore, the spacer 38 ensures a minimum spacing of the radiation source 36 from the skin of a patient in order to exclude an endangerment of the patient by too high a radiation power. For cooling, the stimulation unit 35 includes passive cooling elements. As a further safety element the stimulation unit 35 has a temperature sensor 39 which allows the determination of a possible overheating of the stimulation unit 35.

Figure 8:
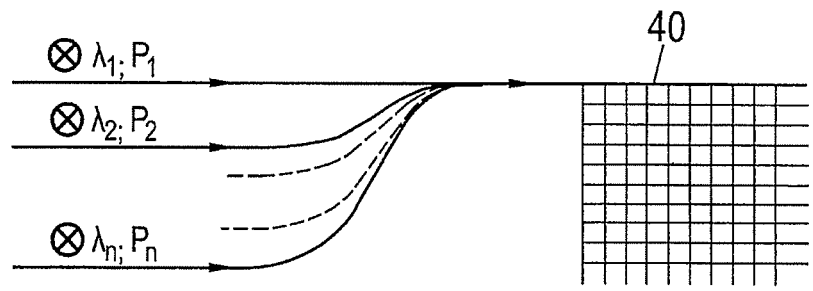
Figure 9:
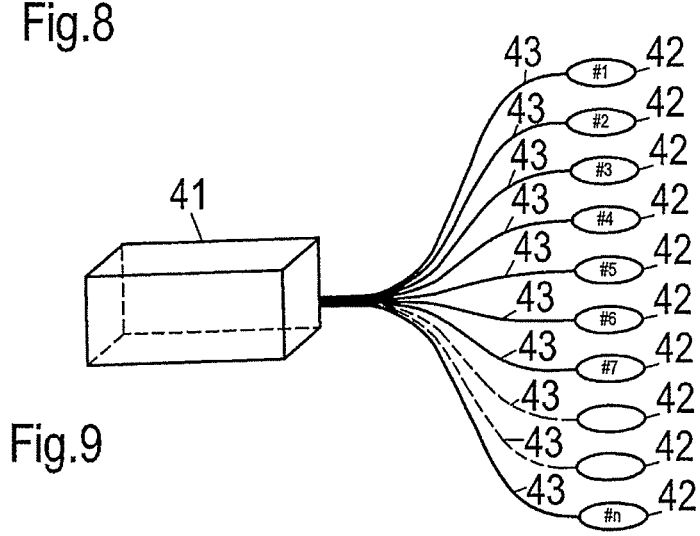
Figure 10:
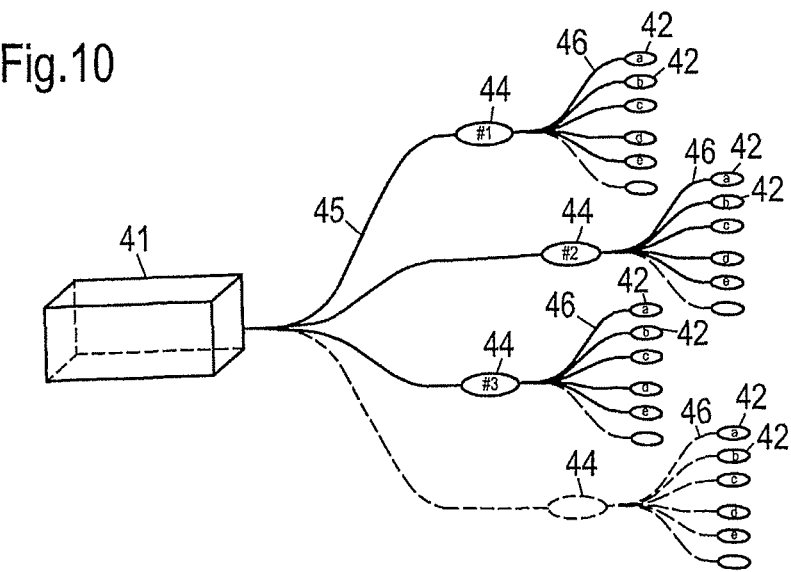

The FIGS. 8 to 10 show embodiments of stimulation units having one or more commonly used radiation sources, e.g. one or more lasers. The radiation emitted by the radiation sources is in this connection guided via the light guide to the stimulation unit.

FIG. 8 shows an embodiment with n radiation sources which respectively generate a radiation of the wavelength $\lambda_i$ and the beam power $P_i$ (with i=1, . . . , n). The different radiations are coupled into a light guide and are guided to a stimulation matrix 40 fastened to the skin of the patient. The different wavelengths $\lambda_i$ have different coefficient of absorptions and for this reason can stimulate different regions of the dermis lying at different depths beneath the skin surface.

FIG. 9 shows a demultiplexer 41, such as is, for example, known from the telecommunication technology, into which the radiation of one of the radiation sources is coupled and which feeds n stimulation units 42. For example one or more adjustable mirrors can be integrated into the demultiplexer 41 which distribute the beam generated by the radiation source to n outputs of the demultiplexer 41, from where the radiation is guided with the aid of light guides 43 to the stimulation units 42. The demultiplexer 41 enables an individual control of each of the stimulation units 42.

It can furthermore be provided that the radiation of M radiation sources is coupled into the demultiplexer 41. The M radiation sources can generate radiation with different wavelengths and/or wavelengths ranges or also with overlapping wavelengths ranges.

A further solution in order to distribute the radiation at a plurality of stimulation units can consists in incorporating a demultiplexer into each stimulation unit, with the demultiplexers guiding the radiation both to the skin of the patient as well as to respectively adjacent stimulation units.

Furthermore, a hybrid solution, such as is shown by way of example in FIG. 10 is plausible. There, splitters 44 are switched between the demultiplexer 41 and the stimulation units 42. The demultiplexer 41 distributes the infrared radiation via lines 45 to the splitter 44 and moreover feeds the splitter 44 via the lines 45 with a supply voltage. The splitter 44 guides the radiation via light guides 46 to the individual stimulation units 42.

Figure 11A:
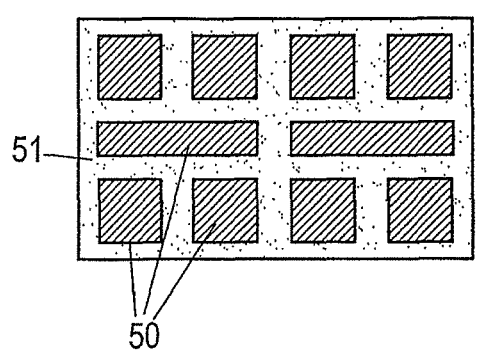
Figure 11B:
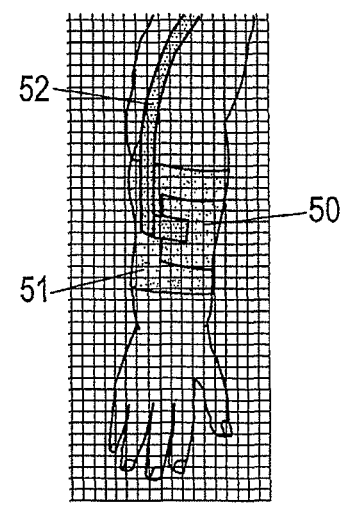

FIGS. 11A and 11B schematically show an apparatus for the stimulation with thermal stimuli in which the stimulation units are configured as organic light emitting diodes (OLEDs) 50. The organic light emitting diodes 50 have a suitable size and are applied at a flexible support 51, which—as is shown in FIG. 11B—can, for example, be fastened to an arm or a leg or to a different body part of the patient. Via one or more supply lines 52 the organic light emitting diodes 50 are connected to a control unit. Each light emitting diode 50 can be individually controlled.

FIGS. 12A to 12D schematically show a further apparatus for the stimulation with thermal stimuli. The apparatus is composed of a plurality of stimulation units 60 which respectively emit electromagnetic radiation towards a skin surface. The stimulation units 60 are of identical design and respectively have a rectangular, in particular quadratic, circumferential profile. At one of the side surface each of the stimulation units 60 has a plug 61 and corresponding sockets 62 at the remaining three side surfaces. Two stimulation units 60 can be mechanically and electrically connected to one another in that the plug 61 of one of the stimulation units 60 is introduced into a socket 62 of one of the other stimulation units 60. In this way an arbitrary amount of stimulation units 60 can be connected to one another and can be adapted to the respective anatomic circumstances of the patient. One of the stimulation units 60 furthermore has a connection cable 63 for the connection to a control unit. It can be provided that this stimulation unit 60 has no plug 61, but rather has sockets 62 arranged at all four side surfaces of the stimulation unit.

Instead of a quadrilateral, in particular rectangular or quadratic, circumferential profile the stimulation units 60 can also have the shape of a different polygon, in particular of a regular polygon, such as e.g. a triangle, a pentagon, an octagon or the like.

The side surfaces of the stimulation units 60 not adjacent to adjacent stimulation units 60 can be occupied with spacers 64. These are, for example, manufactured from plastic or from a different electrically insulating material. A side surface of the spacers 64 is respectively configured in the shape of a plug and in this way can be fastened to the socket 62 of a stimulation unit 60. The spacers 64 create a defined spacing between the lower sides of the stimulation units 60 and the skin of the patient at which the stimulation units 60 should be applied and thereby passively limit the maximum power density (avoidance of skin burns).

A plurality of light emitting diodes 65 are arranged as radiation sources at the lower side of each of the stimulation units 60. The light emitting diodes 65 in particular emit infrared radiation during their operation. In accordance with an embodiment each of the light emitting diodes 65 can be individually controlled. It can alternatively also be provided that the light emitting diodes 65 are grouped together in different groups and that the light emitting diodes 65 respectively of one group receive the same control signal.

Each stimulation unit 60 is electrically connected to the control unit via the stimulation units respectively switched there between. The control unit supplies a stimulation unit 60 with a supply voltage besides the control signals. Alternatively, the control can also be completely or at least partly integrated into the stimulation unit 60. Furthermore, it is plausible that the control unit has the outer shape of a stimulation unit 60 (or at least a similar shape) and is connected to the stimulation units 60 via a plug connection, this means that, in this case, the control unit is fastened together with the stimulation units 60 to the skin of the patient during the operation.

Figure 12A:
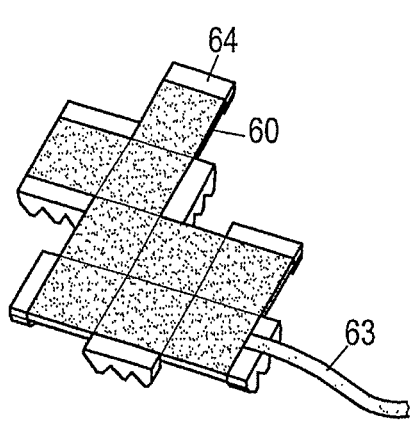
Figure 12B:
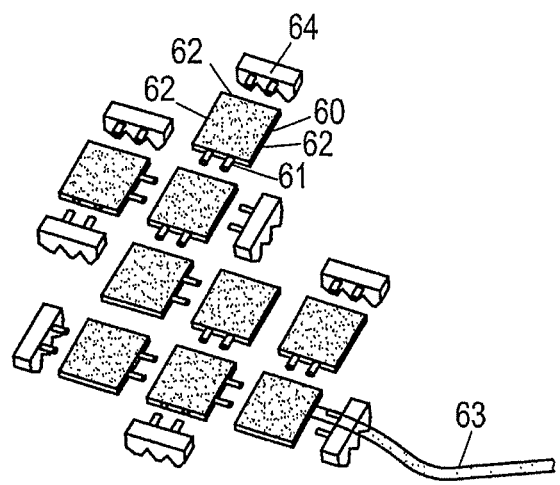
Figure 12C:
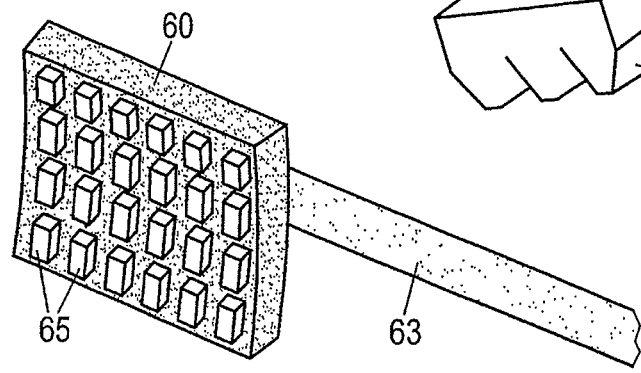
Figure 12D:
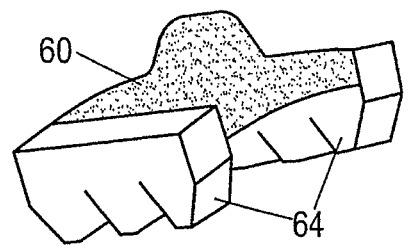

The modular concept of the stimulation apparatus illustrated in FIGS. 12A and 12B permits an arbitrary surface of the skin of the patient to be covered with stimulation units 60.

It can furthermore be provided that stimulation units 60 having different radiation spectra can be made available. Prior to the start of the therapy, the stimulation units 60 can be selected with the ideal radiation spectrums for each patient. Furthermore, it is plausible that a patient can receive therapy at different positions of the skin using stimulation units which emit radiation of different wavelengths ranges due to a different state of the skin at different positions of the skin.

Figure 13A:
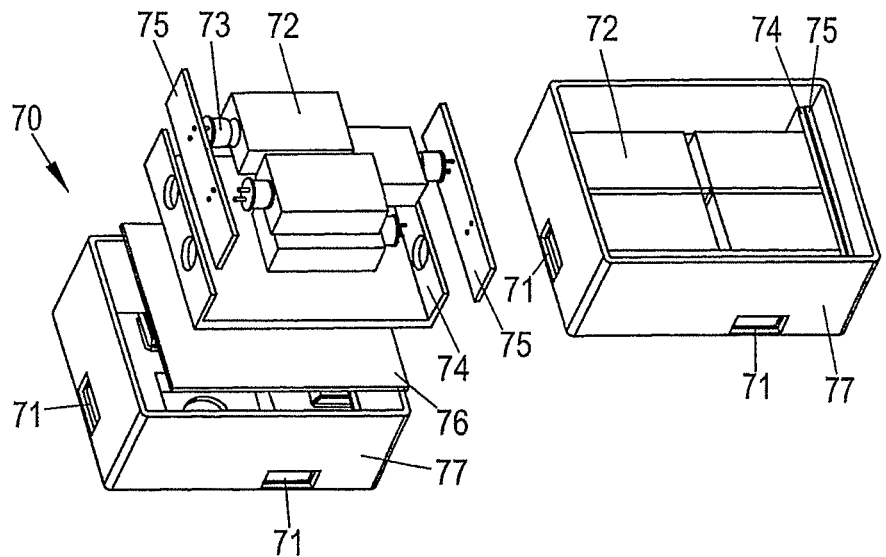
Figure 13B:
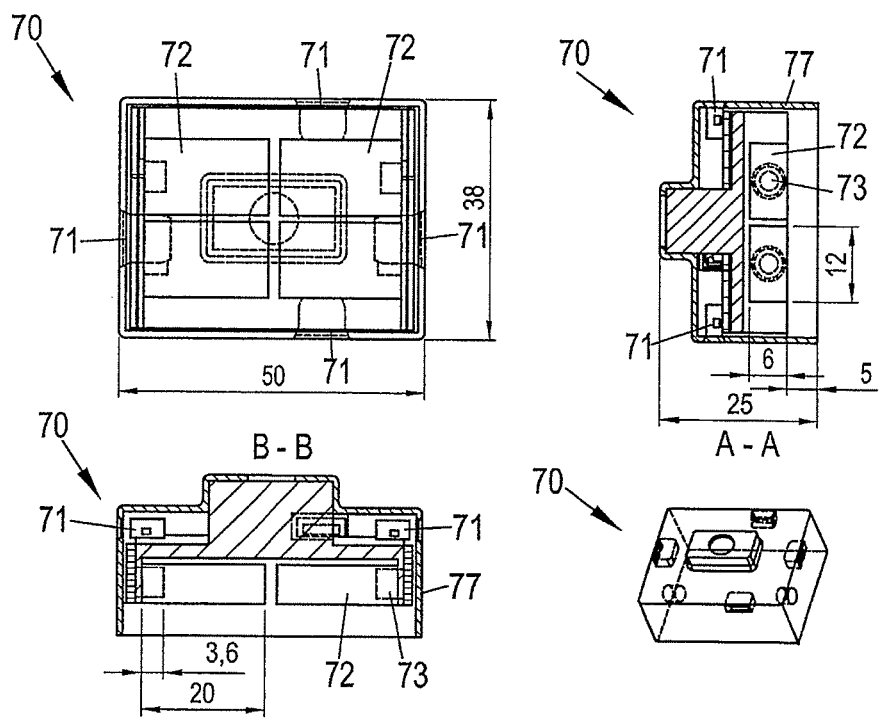

FIGS. 13A and 13B show a stimulation unit 70 as a variant to the stimulation unit 60 of FIGS. 12A to 12D. The stimulation unit 70 has a rectangular circumferential profile, wherein a socket 71 is arranged at each side surface of the stimulation unit 70.

Four plates 72 scattering the radiation are present in the stimulation unit 70. A light emitting diode 73 is integrated into a corresponding cutout of each of the plates 72. Apart from the lower sides of the plates 72 all of other surfaces of the plates 72 can be reflecting. The lower sides of the plates 72 are permeable for the radiation generated by the light emitting diode 73.

The plates 72 are accommodated together with the light emitting diodes 73 in a metal housing 74 which also serves as a heat sink. Furthermore, two light emitting diodes 73 are respectively mounted at an electronic circuit board 75. The metal housing 74 has bores through which the light emitting diodes 73 can be pushed into the cutouts of the respective plates 72. Moreover, a further electronic circuit board 76 is provided at which components for the control of the light emitting diodes 73 and the socket 71 are mounted.

All previously described components are incorporated into a housing 77 which is open to the lower side. The housing 77 is fastened to the skin of the patient with its lower side during the operation of the stimulation unit 70. Due to the shape of the housing 77 and the arrangement of the plates 72 in the housing 77 a defined spacing between the plates 72 and the skin of the patient is created.

Different sections through the stimulation unit 70 as well as a perspective view of the stimulation unit 70 are shown in FIG. 13B. There, exemplary dimensions are stated in millimeters.

The radiation generated by the light emitting diodes 73 which can in particular be infrared radiation in a suitable wavelength range, is diffusely scattered by the plate 72. The lower sides of the plates 72 represent homogeneous radiation surfaces.

A plurality of stimulation units 70 can be connected to one another just like the stimulation unit 60 shown in FIGS. 12A and 12B. Since the stimulation units 70, however, have no plug in contrast to the stimulation units 60, two adjacent stimulation units 70 are electrically and mechanically connected to one another by means of a plug connector which engages into the respective socket 71 of the two stimulation units 70.

In the following, thermal stimuli which can be generated with the stimulation units described in this application are described. Such thermal stimuli can also be found in the German patent application no. 10 2010 000 390.5 having the title "Vorrichtung und Verfahren zur Behandlung eines Patienten mit Vibrations-, Tastund/oder Thermoreizen (apparatus and method for the treatment of a patient with vibration stimuli, tactile stimuli and/or thermal stimuli) which was filed at the German Patent and Trademark Office on Feb. 11, 2010. The complete content of disclosure of the German patent application no. 10 2010 000 390.5 is hereby incorporated into the disclosure of the present application.

Figure 14:
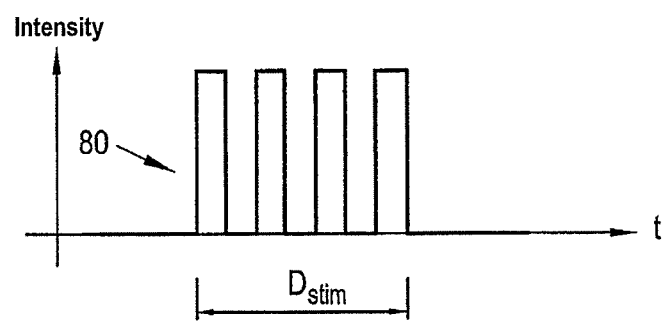

FIG. 14 shows a thermal stimuli 80 having a stimulation duration $D_{stim}$, whereas the radiation generated by the stimulation unit is periodically varied with the frequency $f_{thermal}=1/T_{thermal}$. The variation can, for example, be generated by the switching on and/or switching off of the radiation source or through a modulation of the radiation constantly emitted by the radiation source. Through the selection of a suitable wavelength, in particular of infrared radiation, the region of the dermis in which the thermal receptors are present is heated.

The stimulation duration $D_{stim}$ of the thermal stimuli 80 can lie in the range of 10 to 2000 ms. The frequency $f_{thermal}$ can lie in a region between 0.01 and 10 Hz or also outside of this range. A temperature of up to 42° C. is generated in the stimulated region of the dermis by means of the thermal stimuli 80.

Instead of pulse-like thermal stimuli also differently designed thermal stimuli, e.g. stimuli patterns continuous in time, such as for example sinus stimuli can be used. The frequency of the sinusoidal oscillations can lie in a range of 0.01 to 150 Hz and in particular in the range of 60 to 150 Hz.

The thermal stimuli applied by the stimulation unit are received by the thermal receptors and are forwarded to the nervous system. Heat receptors (also known as warm receptors, heat sensors or warm sensors) count as thermal receptors and cold receptors (also known as coldness receptors, cold sensors or coldness sensors) also count as thermal receptors.

The thermal stimulation described in this context can, in particular be used for the treatment of neurological or psychiatric pathologies, e.g. Morbus Parkinson, essential tremors, tremors as a consequence of Multiple Scleroses, as well as different pathological tremors, dystonia, epilepsy, depression, motor disorders, cerebellar diseases, obsessive compulsive disorders, Tourette syndrome, autism, functional interferences following a stroke, functional interferences following a brain injury, spastics, tinnitus, sleep disorders, schizophrenia, addictive disorders, borderline character disorders, attention deficit disorders, attention deficit hyperactivity disorders, compulsive gambling, neuroses, craving for food, anorexia, eating disorders, burnout syndrome, fibromyalgia, migraines, cluster headaches, general headaches, tension headaches, neuropathic pain, chronic pain states, neuralgia, amputation pain, ataxia, tic defects or hypertonia, as well as further diseases which are characterized by a pathologically increased neuronal synchronization. However, also gastrointestinal diseases, such as e.g. irritable colon syndrome can be treated. Hereby painful cramps and/or inefficient intestinal motility can be unlearned. Also with regard to colitis ulcerose and on Morbus Crohn the thermal stimulation can act to release cramps and as a pain relief. Furthermore, asthma bronchioles, COPD (chronic obstructive lung diseases), cardiac ischemia, as well as the peripheral arterial occlusive disease can be treated.

The previously mentioned diseases can be caused by an interference of the bioelectric communication of neural networks which are connected to one another in specific circuits. Hereby a neuron population generates a continuously pathological neuronal activity and possibly a pathological connectivity (network structure) associated therewith. In this connection a large number of neurons form synchronous action potentials, this means that the associated neurons fire excessively synchronously. Moreover, this fact means that the pathological neuron population has an oscillatory neuronal activity, this means that the neurons fire rhythmically. In the case of neurological or psychiatric diseases the mean frequency of the pathological rhythmic activity of the associated neural network for example lies in the range of 1 to 30 Hz, but can also lie outside of this range. For healthy people the neurons in contrast trigger in a different qualitative manner, e.g. in an uncorrelated manner.

Having regard to the thermal stimulation in accordance with the invention, the thermal stimuli administered to the patient are received by the thermal receptors and from there are forwarded via the nervous system to a pathologically active neuron population in the brain and/or in the spinal cord. The thermal stimuli are configured in such a way that the pathologically synchronous activity of the neuron population is desynchronized. A reduction of the rate of coincidence of the neurons brought about by the stimulation can lead to a reduction of the synaptic weight and thus to an unlearning of the tendency of the production of pathologically synchronous activity.

The targeted stimulation of certain regions of the brain or of the spinal cord is enabled by the somatotopic association of body regions with respect to these regions. For example, the stimulation elements can be attached at the foot, the lower leg, and the upper leg or, however, at the hand, the lower arm and the upper arm of the patient. Due to the somatotopic structuring of the nerve conductor tracks, different neurons are stimulated by the stimuli applied at the respective positions. The somatotopic association of skin regions with regions of the brain is, for example, described in A. Benninghoff et al.: "Lehrbuch der Anatomie des Menschen. Dargestellt unter Bevorzugung funktioneller Zusammenhänge. 3. Bd. Nervensystem, Haut und Sinnesorgane" (Textbook of the anatomy of the human. Illustrated with respect to preferred functional associations. $3^{rd}$ edition. Nervous system, skin and sensory organs) published by Urban und Schwarzenberg, Munich 1964.

Through the use of a plurality of stimulation units placed at different positions at the skin different regions of the brain or of the spinal cord can thus be separately stimulated in that the applied thermal stimuli are forwarded via nerve lines to different target regions which lie in the brain and/or the spinal cord. The target regions can be stimulated during the thermal stimulation with possibly different stimuli or time shifted stimuli.

Having regard to a variant of the thermal stimulation the coordinated reset (CR) stimulation, which is characterized by large therapeutic effectivity and safety (cf. e.g. "A model of desynchronizing deep brain stimulation with a demand-controlled coordinated reset of neural subpopulations" by P. A. Tass published in Biol. Cybern. 89, 2003, pages 81 to 88), thermal stimuli are administered to a neuron population which has a pathologically synchronous and oscillatory activity, which stimuli bring about a reset in the neuron population, a so-called reset of the phase of the neural activity of the stimulated neurons. Through the reset of the phase of the stimulated neurons is set independent of the current phase value, to a phase value lying at or near to a specific phase value of e.g. 0° (in practice it is not possible to exactly set a certain phase value, however, this is also not required for a successful CR stimulation). Thus, the phase of the neuronal activity of the pathological neuron population is controlled by means of a targeted stimulation. As it is furthermore possible to stimulate the pathological neuron population at different positions, the phase of the neural activity of the pathological neuron population can be reset at the different stimulation positions at different points in time. As a result the pathological neuron population, whose neurons were previously synchronous and active with the same frequency and phase, can thereby be split into a plurality of subpopulations. Within one of the subpopulations the neurons are still synchronous and further still trigger with the same pathological frequency after the reset of the phase, but each of the subpopulations has the phase with respect to its neuronal activity which was imposed thereon by means of the stimulation stimuli. This means that the neuronal activity of the individual subpopulations still has an approximately sinusoidal extent with the same pathological frequency after the reset of their phases, but has different phases.

Due to the pathological interaction between the neurons the state generated through the stimulation having at least two subpopulations is instable and the complete neuron population quickly approximates to a state of complete desynchronization in which the neurons trigger in an uncorrelated manner. The desired state, this means the state of complete desynchronization, is thus not immediately present after the time delayed (or phase displaced) application of the phase resetting thermal stimuli, but is frequently set within a few periods or in less than a period of the pathological frequency.

A theory for the explanation of the stimulation success is based thereon that the finally desired desynchronization by means of the pathologically increased interaction between the neurons is firstly enabled. Hereby a self-organization process is used which is responsible for the pathological synchronization. The same brings about the effect that a division of an overall population into subpopulations with different phases follows a desynchronization. In contrast thereto no desynchronization would take place without a pathologically increased interaction of the neurons.

Moreover, a new organization of the connectivity of the pathological neuronal network can furthermore be achieved by the CR stimulation, so that a persistent therapeutic effect can be brought about. The achieved synaptic conversion is of larger importance for the effective treatment of neurological or psychiatric diseases.

Figure 15:
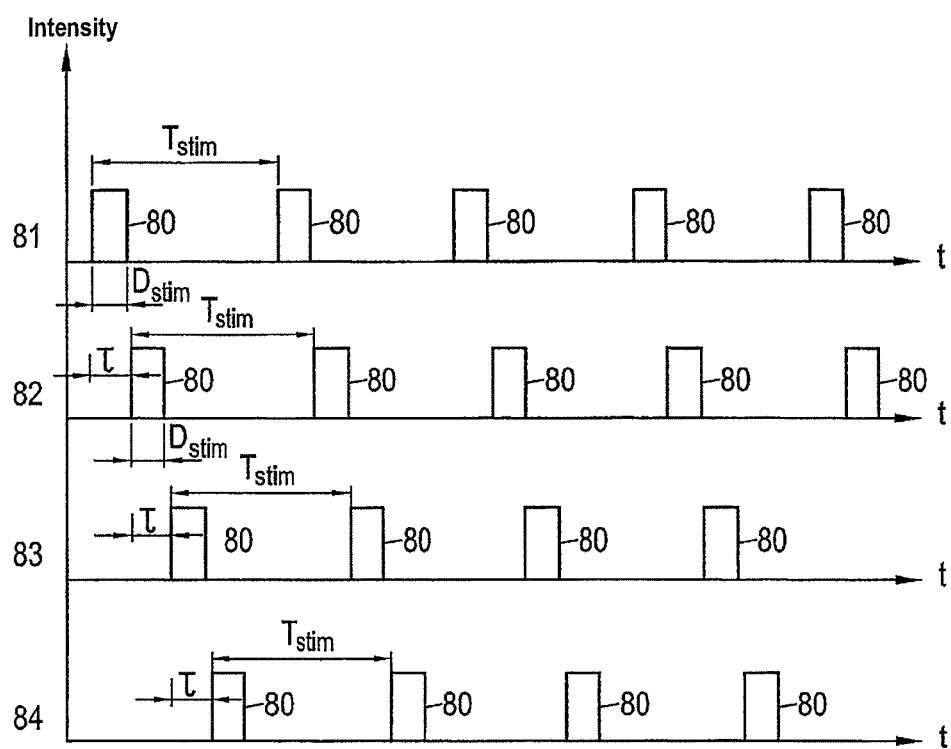

In FIG. 15 a CR stimulation is schematically illustrated which is carried out with four stimulation units 81 to 84. With the aid of the stimulation units 81 to 84 the respective thermal receptors are stimulated at different positions of the skin of the patient with the thermal stimuli 80 illustrated in FIG. 14.

Having regard to the embodiment illustrated in FIG. 15 each of the stimulation units 81 to 84 applies thermal stimuli 80 periodically with the frequency $f_{stim}=1/T_{stim}$. The frequency $f_{stim}$ can lie in the range of 0.1 to 60 Hz and in particular in the range of 30 to 60 Hz or in the range of 1 to 30 Hz or in the range of 1 to 20 Hz or in the range of 5 to 20 Hz, however, can also take on smaller or larger values. In particular the frequency $f_{stim}$ can lie near the mean frequency of the pathologically rhythmic activity of the target network.

The administration of the thermal stimuli 80 via different stimulation units 81 to 84 takes place with a delay in time between the individual stimulation units 81 to 84 by $T_{stim}/4$.

In the case of N stimulation units the delay in time τ between two thermal stimuli 80 respectively following one another can, for example, lie in the range of any Nth of the period of $1/f_{stim}$, this means $1/(N \times f_{stim})=T_{stim}/N$. In this case, the time $T_{stim}/N$ can subsequently lapse between the starting points of two thermal stimuli 80 following one another. One can deviate from the provision that the delay in time τ between two consecutive thermal stimuli amounts to $T_{stim}/N$ to a certain degree. For example, one can deviate by up to ±5%, ±10% or ±20% for the delay in time τ from the value $T_{stim}/N$. Having regard to such deviations stimulation cells could still be achieved, this means that a desynchronizing effect could still be observed.

The thermal stimuli 80 applied by the stimulation units 81 to 84 are forwarded to different subpopulations of the pathologically synchronous neuron population and reset the phase of these subpopulations to respectively different points in time, whereby a desynchronization of the overall neuron population is achieved.

Having regard to the therapy different kinds of the CR stimulation can be used. A possibility consists in an "N of N" CR stimulation, this means that thermal stimuli 80 are applied by all N stimulation units per stimulation cycle $T_{stim}$, like in FIG. 15 (for N=4). Alternatively also an "L from N" CR stimulation (with L<N) can be carried out, during which L of N stimulation units are e.g. randomly selected per stimulation cycle $T_{stim}$ and the thermal stimuli 80 are applied by these. In this way, a larger spatial variability can be generated.

Further variations of the CR stimulation with four stimulation units (N=4) are shown in the FIGS. 16 and 17.

FIG. 16 shows a pause which can be provided during the application of the thermal stimuli 80 and during which no stimulation takes place. Such pauses can be selected of arbitrary length and can in particular amount to a whole number multiple of the period $T_{stim}$. Furthermore, the pauses can be maintained after an arbitrary number of stimulations. For example, a stimulation can be carried out during P periods of the length $T_{stim}$ following one another and subsequently a pause during Q periods of the length $T_{stim}$ without stimulation can be maintained, wherein P and Q are smaller whole numbers, e.g. in the range of 1 to 20. This scheme can either be periodically continued or stochastically and/or deterministically modified e.g. chaotically modified.

A further possibility of deviating from the strongly periodic stimulation pattern shown in FIG. 15 consists therein in varying the timely sequence of the thermal stimuli 80 stochastically or deterministically or mixed stochastic deterministically. FIG. 17 shows that the sequence in which the individual stimulations units apply the thermal stimuli 80 per period $T_{stim}$ (or also in different steps of time) is varied. This variation can take place stochastically or deterministically or mixed stochastic-deterministically.

The randomization shown in FIG. 17 can be combined with the stimulation shape shown in FIG. 16. For example, a renewed randomization can be carried out in each of the P stimulation sections of the length $T_{stim}$ following one another or, however, after each pause of the length $Q \times T_{stim}$ a randomization takes place and within the following P stimulation time section the sequence in which the stimulation units apply the thermal stimuli 80 remains constant.

Furthermore, a deviation from the strongly periodic stimulation pattern shown in FIG. 15 can be deviated from, in that the delay in time between two consecutive thermal stimuli 80 is not always of equal size. It can be provided that the spacing in time between the thermal stimuli 80 can be selected differently. Furthermore, the delay times can also be varied during the treatment of a patient. The delay times with regard to the physiological signal propagation times can also be adjusted.

The stimulation effects achieved by the application of thermal stimuli described in this application can be controlled with the aid of sensors which measure the neuronal activity in the stimulated target region or in a region connected to the target region. Non-invasive sensors can be used as sensors, e.g. electroencephalographic (EEG) electrodes, magnetoencephalographic (MEG) sensors, sensors for the measurement of a local field potentials (LFP) and electrocardiogram sensors (ECG) sensors can be used. The neuronal activity can also be determined indirectly through the measurement of the muscle activity associated therewith by means of electromyography (EMG).

Alternatively, the sensors can be implanted into the body of the patient. For example epicortical electrodes, depth brain electrodes, subdural or epidural brain electrodes, subcutaneous EEG electrodes and subdural or epidural spinal cord electrodes can, for example, serve as invasive sensors. Furthermore, electrodes to be fastened to the peripheral nerves can be used as sensors.

With the aid of the sensors the mean frequency of the pathological rhythmic activity of the target network can further be measured. The frequency $f_{stim}$ of the CR stimulation can be adapted to the measured frequency. Preferably, this frequency adaptation takes place automatically and due to the fact that the apparatus in accordance with the invention has means for signal analysis of the measurement signals measured by the sensors. In this way e.g. the heart rate variability (HRV) can be determined from the ECG. Through the extraction of the characteristic rhythms of the HRV physiologically vegetative rhythms can be amplified and/or pathological rhythms can be desynchronized by means of the apparatus in accordance with the invention.

The invention claimed is:

1. An apparatus for stimulating thermal-receptors lying in the skin of a patient with thermal stimuli, the apparatus comprising:
    a plurality of non-invasive stimulation units configured to irradiate the skin of the patient with electromagnetic radiation and generate thermal stimuli in the skin of the patient by absorbing the electromagnetic radiation, wherein the stimulation units respectively have a main surface at which the electromagnetic radiation is emitted and a plurality of side surfaces;
    a plurality of connection elements provided at the plurality of side surfaces, wherein the stimulation units can be connected to one another via the connection elements, with each stimulation unit having a first connection element that is a plug at one side surface and second connection elements that are sockets at all remaining side surfaces, such that the first and the second connection elements are structurally configured to engage within one another to produce a connection; and a plurality of spacers that each have a plug at one side surface that can be mechanically connected to a socket of only one of the stimulation units, wherein each of the spacers protrudes a distance from the main surface in order to create a spacing between the main surface of the stimulation units and the skin of the patient, wherein the plurality of spacers are configured to be connected to an array of the plurality of stimulation units when the plurality of stimulation units are directly connected to each other via the first and second connection elements.

2. The apparatus in accordance with claim 1, wherein a mechanical and electrical connection of the stimulation units is produced by the connection elements.

3. The apparatus in accordance with claim 1, wherein exactly one of the stimulation units has a connection cable for the connection to a control unit, with the exactly one stimulation unit having sockets at all side surfaces and no plug.

4. The apparatus in accordance with claim 1, wherein a peripheral profile of each of the stimulation units formed by the side surfaces has the shape of a regular polygon.

5. The apparatus in accordance with claim 4, wherein the peripheral profile of each of the stimulation units formed by the side surfaces has the shape of one of a rectangle and a square.

6. The apparatus in accordance with claim 1, wherein at least two of the stimulation units are configured to produce electromagnetic radiation with at least partly different wavelengths.

7. The apparatus in accordance with claim 6, wherein the stimulation units can be selected based on a desired penetration depth of the electromagnetic radiation into the skin of the patient.

8. The apparatus in accordance with claim 1, wherein the stimulation units respectively have a plurality of plates controlling the radiation and a light emitting diode is integrated into a cutout of each plate.

9. The apparatus in accordance with claim 8, wherein the surfaces of the plates which are disposed facing the skin of the patient are transparent with respect to the electromagnetic radiation generated by the light emitting diode and all other surfaces of the plates are reflecting with respect to the electromagnetic radiation generated by the light emitting diode.

* * * * *